US008398859B2

(12) United States Patent
Del Cañizo López

(10) Patent No.: US 8,398,859 B2
(45) Date of Patent: Mar. 19, 2013

(54) HAEMODIALFILTRATION METHOD AND APPARATUS

(75) Inventor: Juan Francisco Del Cañizo López, Madrid (ES)

(73) Assignee: Fundacion Para la Investigacion Biomedica del Hospital Gregorio Maranon, Madrid (ES)

( * ) Notice: Subject to any disclaimer, the term of this patent is extended or adjusted under 35 U.S.C. 154(b) by 289 days.

(21) Appl. No.: 12/596,154

(22) PCT Filed: Apr. 23, 2007

(86) PCT No.: PCT/ES2007/070081
§ 371 (c)(1),
(2), (4) Date: Mar. 31, 2010

(87) PCT Pub. No.: WO2008/129084
PCT Pub. Date: Oct. 30, 2008

(65) Prior Publication Data
US 2010/0187176 A1      Jul. 29, 2010

(51) Int. Cl.
*B01D 61/32* (2006.01)
*B01D 61/28* (2006.01)
(52) U.S. Cl. ............ 210/646; 210/97; 210/98; 210/117; 210/143; 210/195.1; 210/195.2; 210/252; 210/257.1; 210/257.2; 210/258; 210/321.6

(58) Field of Classification Search .................... 210/97, 210/98, 117, 143, 195.1, 195.2, 252, 257.1, 210/257.2, 258, 321.6, 645, 646
See application file for complete search history.

(56) References Cited

U.S. PATENT DOCUMENTS

| 4,997,570 A | 3/1991 | Polaschegg |
| 5,011,607 A | 4/1991 | Shinzato |
| 2004/0068219 A1* | 4/2004 | Summerton et al. ......... 604/5.01 |
| 2005/0131332 A1* | 6/2005 | Kelly et al. .................. 604/4.01 |

FOREIGN PATENT DOCUMENTS

| EP | 0516152 A1 | 12/1992 |
| EP | 1342479 A1 | 9/2003 |
| WO | 02/36247 A1 | 5/2002 |
| WO | 02/062454 A1 | 8/2002 |

* cited by examiner

*Primary Examiner* — John Kim
(74) *Attorney, Agent, or Firm* — Ladas & Parry LLP

(57) ABSTRACT

Device for haemodiafiltration, which comprises a first circuit for a dialysis solution and a second circuit for blood, so that the toxic substances from the blood flow pass into the dialysis liquid within a haemofilter (11), a liquid pump (20) located upstream of the haemofilter (11) in the first dialysis liquid circuit, is adapted for injecting replacement liquid into the dialysis solution flow after a blood pump (15) finishes pumping blood to the interior of the haemofilter (11).

11 Claims, 2 Drawing Sheets

HAEMODIALFILTRATION METHOD AND APPARATUS

PURPOSE OF THE INVENTION

This invention refers to a method and device for performing haemodiafiltration, which is a renal dialysis method that combines haemodialysis and haemofiltration, in order to achieve a high removal of substances with a high and low molecular weight.

STATUS OF THE TECHNIQUE

From patent EP0516152B1, a device is known for performing haemodiafiltration, namely, an extra-renal purification technique that combines two mechanisms: dialysis or diffusion and ultrafiltration or convection.

The aforementioned device comprises two circuits; a dialysis liquid is connected to a first circuit through the external chamber of a haemofilter against the direction of the blood flow, which is connected to a second circuit to maximize the difference in concentration of the substances that one wishes to remove, in all areas of the filter.

Therefore, a dialysis liquid is infused into the haemofilter against the flow, which will be removed with the ultra-filtering.

Consequently, a path of solutes with low molecular weight takes place from the blood to the dialysis liquid due to the difference in concentration, in addition to a high clearance of water and solutes by the pressure gradient. In other words, it filters blood, extracts liquid from the internal media, dialyses and purifies solutes from the body.

The first circuit of the dialysis solution is regulated by a set of pumps located upstream and downstream of the haemofilter, respectively.

Analogously, the second circuit of the blood is also regulated by a set of pumps located upstream and downstream of the haemofilter, respectively.

The replacement liquid can be infused in the arterial line, upstream of the haemofilter, pre-dilution, and in the vein line that exits from the haemofilter, post-dilution.

Generally, the method most used is post-dilution. However, this method has some disadvantages, such as the blood in the haemofilter becoming very concentrated when a high amount of liquid is extracted.

A consequence of the above is that the performance of ultra-filtering decreases and an increase occurs in the resistance to the path of the blood flow, which may lead to a poor flow and the clotting of the second blood circuit; since the rate of haemofiltration rises, the blood becomes concentrated in the haemofilter, its viscosity increases and the hydraulic resistance and risk of clotting of the same increases.

A consequence of the above is that the service life of the haemofilter is reduced.

CHARACTERIZATION OF THE INVENTION

This invention seeks to resolve and reduce one or more of the problems stated above, through a haemodiafiltration device as is claimed in claim 1. Embodiments of the invention are established in the subsequent claims.

A purpose of this invention is to extend the service life of the haemofilter and avoid the decreased performance of the same during its effective lifetime.

Another purpose of this invention is to decrease the risk of blood clotting in the second blood circuit of the haemodiafiltration device.

Yet another purpose of this invention is to decrease the risk of obstruction of the filtering media, the semipermeable membrane, which separates the two flows that enter and leave the haemofilter.

BRIEF DESCRIPTION OF THE FIGURES

Now the devices that make up the invention will be described, as an example only, referring to the attached drawings, in which.

DESCRIPTION OF THE INVENTION

Figure 1:
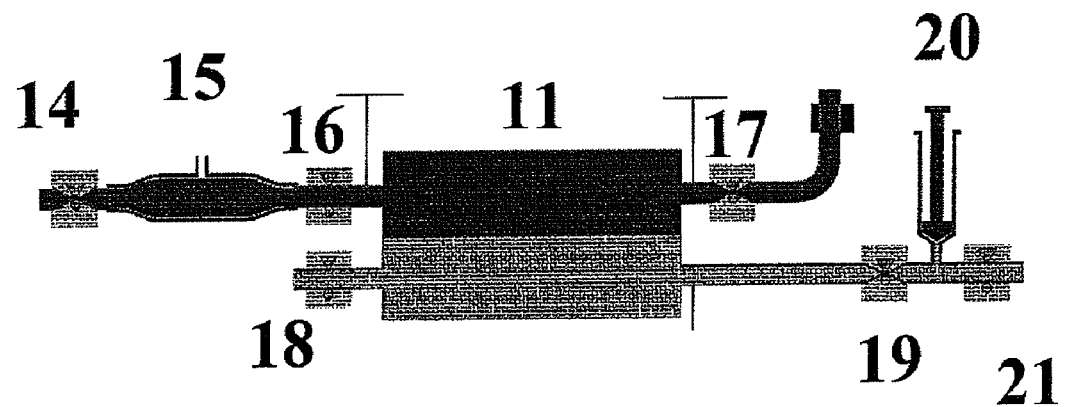
FIG. 1 shows in a flow chart a haemodiafiltration device according to the invention.
Figure 2:
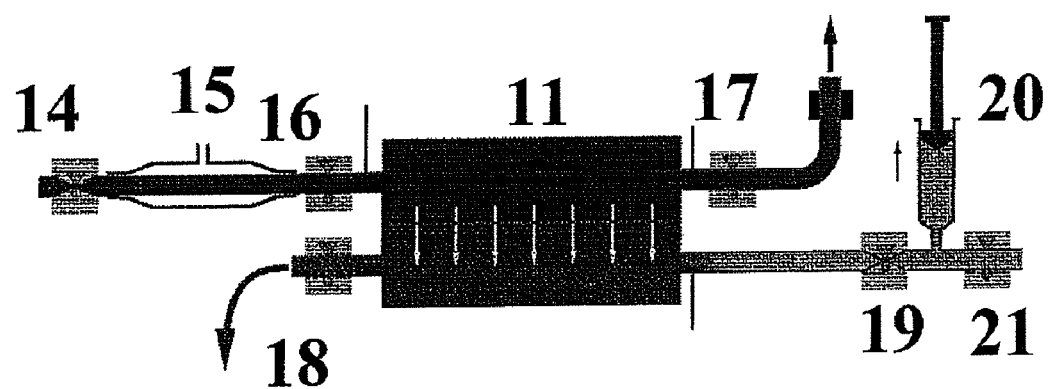
FIG. 2 shows when a blood pump of the haemodiafiltration device is empty according to the invention.
Figure 3:
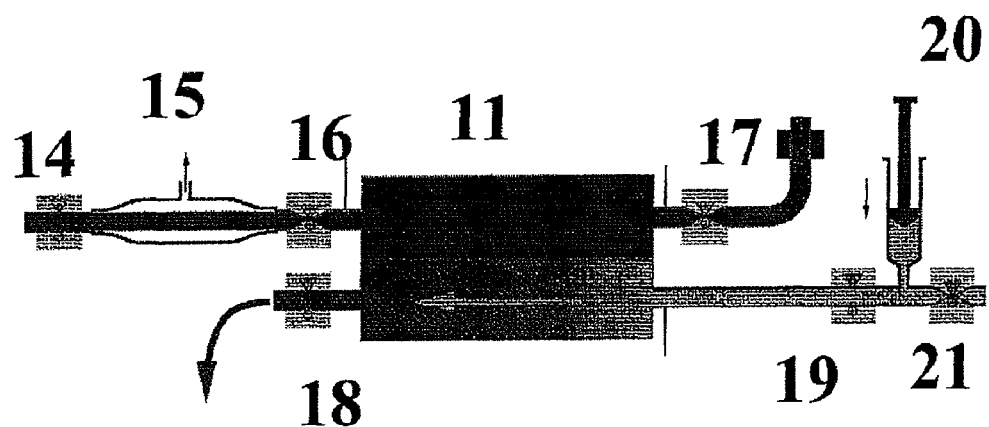
FIG. 3 shows when a liquid pump of the haemodiafiltration device injects the fill liquid into the dialysis liquid circuit according to the invention.
Figure 4:
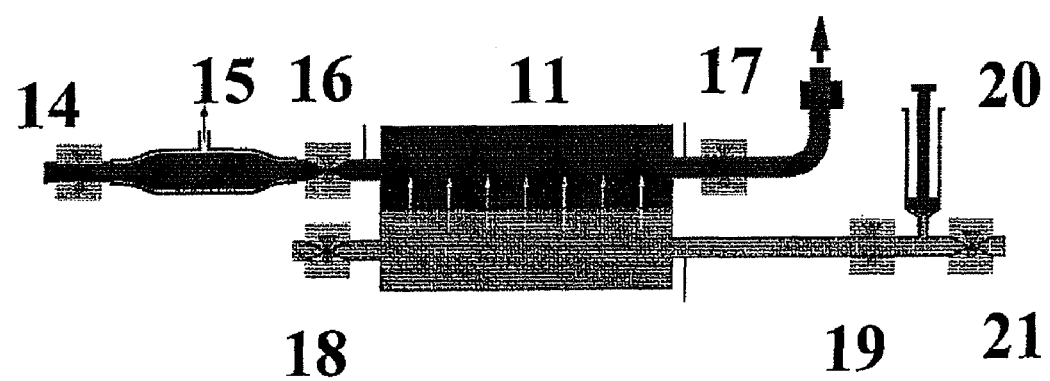
FIG. 4 shows the blood pump of the haemodiafiltration device full according to the invention.

In reference to FIG. 1, below there is a flow chart schematically illustrated of a device used to perform haemodiafiltration, which comprises a first circuit of the dialysis solution regulated by the action of a first set of valves 18, 19, 21 and a pump 20 just like a syringe tube pump 20, which is located upstream of the first dialysis circuit, i.e. before a haemofilter 11.

A second regulated blood circuit, also regulated by the action of a second set of valves 14, 16, 17 and a pump 15, just like a tube pump 15, which is located on the upstream side, i.e. the arterial side of the second blood circuit before the haemofilter 11.

Both the first and second circuit come into contact at the haemofilter 11, which comprises a semipermeable membrane.

As has been mentioned previously, each circuit comprises at least three valves 18, 19, 21, 14, 16 and 17, respectively, distributed upstream and downstream of haemofilter 11.

Replacement liquid is injected through syringe pump 20, the reinfusion process, of a solution that can be similar to the dialysis solution in the blood through haemofilter 11 to re-establish to its original volume.

To carry out reinfusion, the pulsating characteristics of the tubular pump 15 are used, which cause the trans-membrane pressure in the membrane of haemofilter 11 during haemofiltration to not be constant, and may become quite absent at any moment.

The aforementioned pressure is highest during the systole of blood pump 15 and practically zero during the diastole of the same.

By taking advantage of this circumstance, one can carry out the reinfusion process of the replacement liquid by using the pressure gradient that is generated in the very membrane of the haemofilter. In other words, during this time period, the flow through the same is inverted, and if in this time period the reinfusion liquid is added to the dialysis solution, said reinfusion liquid passes into the blood flow, since the flow through the membrane is inverted, i.e. a liquid path from the dialysis solution to the blood flow takes place.

Based on FIGS. 1 to 4, we can explain the replacement liquid path process to the blood flow through the haemofilter 11 membrane.

The starting situation is when the blood pump 15 is completely full, the second outlet valve 16 is open and the third blood stop valve 17 after haemofilter 11 is closed.

Simultaneously, the liquid perfusion pump 20 is completely empty and the second outlet valve 19 is closed, with the first replacement liquid stop valve 21 being open.

Under these conditions, the impulse of the blood pump 15 takes place. The volume moved by the aforementioned pump 15 enters the blood chamber of haemofilter 11 and an equivalent volume of plasma seeps through the membrane of the same and exits the liquid outlet of the haemofilter through the third valve 18.

This plasma outlet causes the blood contained in haemofilter 11 to become concentrated as a function of the relationship that exists between the ejection volume of blood pump 15 and the blood chamber volume of haemofilter 11. See FIG. 2.

During the impulse process of blood pump 15, the replacement liquid pump 20 has been filled with replacement liquid.

At that time, the blood inlet valve 16 and outlet valve 17 of the filter are closed and the replacement liquid inlet valve 19 and outlet valve 18 of the haemofilter are open, with the impulse of liquid pump 20 starting, which at this first moment is used to wash the dirty liquid that was just filtered. See FIG. 3.

Once a pre-determined volume of liquid has passed from the scheduled wash, the third replacement liquid outlet valve 18 is closed and the third blood outlet valve 17 of the haemofilter opens.

The remaining volume of liquid moved by liquid pump 20, upon finding itself with the closed first liquid stop valve 21 and the third replacement liquid outlet valve 18, seeps towards the blood flow through the membrane in the reverse direction.

If the volume that is injected with liquid pump 20 is substantially similar to the volume of plasma that has been previously ultra-filtered, the blood will recover its original haematocrit within the same haemofilter 11 and at the same time, an equivalent volume of blood will be replaced for the patient. See FIG. 4.

Some advantages of the system are that the blood does not increase its haematocrit within the capillary of haemofilter 11, and therefore the hydraulic resistance of the same is lower.

As the haematocrit does not increase in the capillary of the haemofilter 11 membrane, the risk of clotting is minimized.

Filtration at the haemofilter 11 membrane is done in the direction of the blood flow towards the dialysis liquid and vice versa, i.e. in both directions of the membrane, whereby it hinders the depositing of platelets and erythrocytes in the pores of the capillary, and therefore the obstruction of the same.

In this device, the direction of filtration at the membrane is inverted in each cycle, with which the depositing of cells is reduced, as is the obstruction of the membrane pores.

The coordinated operation of both pumps 15, 20 and of the six valves 15 to 19 and 21 is controlled and regulated by a control unit that receives information from a set of receivers distributed over pumps 15, 20 and the six valves 15 to 19 and 21.

Said control unit is adapted to perform a variation calculated at the flow of each of the pumps 15 and 20 respectively, in such a way that it allows the opening and closing time of each of the valves to be regulated so that the liquid added to the dialysis solution passes into the blood flow.

The embodiments and examples stated in this report are presented as the best explanation of this invention and its practical application, and thus allow the experts in the technique to put into practice and utilise the invention. However, the experts in the technique will recognise that the description and the above examples have been presented for the purpose of illustration and as an example only. The description as explained is not intended to be exhaustive or to limit the invention to the exact described form. Many modifications and variations are possible in light of the above instruction without going beyond the intent and scope of the following claims.

The invention claimed is:

1. A hemodiafiltration device comprising a hemofilter, a first circuit for circulating a dialysis liquid through the hemofilter in a first direction of flow; a second circuit for circulating blood through the hemofilter in a second direction of flow; a liquids pump for injection of a substitution liquid into the first circuit so that the substitution liquid can be circulated through the hemofilter together with the dialysis liquid, said liquids pump being disposed upstream of the hemofilter with reference to the first direction of flow; a blood pump for injecting blood through the second circuit into the hemofilter, said blood pump being disposed upstream of the hemofilter with reference to the direction of flow of blood; said hemofilter comprising a semi-permeable membrane that separates blood in the second circuit from dialysis liquid in the first circuit; and means for selectively opening and closing the respective first and second circuits upstream and downstream of the hemofilter to enable generation in the hemofilter of either (i) a first pressure gradient, wherein toxic substances from the blood in the second circuit flow through the membrane into the dialysis liquid, or (ii) a second pressure gradient, wherein the substitution liquid injected by the pump into the first circuit flows through the membrane into the blood in the first circuit, wherein for generation of the second pressure gradient, the second circuit is closed upstream of the hemofilter and open downstream of the hemofilter with reference to the direction of flow of blood, and the first circuit is open upstream of the hemofilter and closed downstream of the hemofilter with reference to the direction of flow of the dialysis liquid, wherein the means comprises a first plurality of valves in the first circuit and a second plurality of valves in the second circuit; and wherein the hemofiltration device comprises a control unit for regulating the respective blood pump, liquids pump, and the first and second plurality of valves so as to control the flow of liquid from the first circuit through the membrane into the blood in the second circuit.

2. The hemodiafiltration device according to claim 1, wherein, when the blood pump injects blood through the second circuit into the hemofilter and the first circuit is closed upstream and open downstream of the hemofilter with reference to the direction of flow of the dialysis liquid and the second circuit is open downstream of the hemofilter with reference to the direction of flow of blood, the first pressure gradient is generated in the hemofilter whereby toxic substances from the blood in the second circuit flows through the membrane into the dialysis liquid in the first circuit.

3. The hemodiafiltration device according to claim 2, wherein for generation of the first pressure gradient, the first circuit is closed upstream and open downstream of the hemofilter with reference to the direction of flow of the dialysis liquid and the second circuit is open upstream and downstream of the hemofilter with reference to the direction of flow of blood.

4. The hemodiafiltration device according to claim 2, including a first valve upstream of the liquids pump, a second valve downstream of the liquids pump and a third valve downstream of the hemofilter with reference to the direction of flow of the dialysis liquid.

5. The hemodiafiltration device according to claim 4, including a first valve upstream of the blood pump, a second valve downstream of the blood pump and a third valve downstream of the hemofilter with reference to the direction of flow of blood.

6. The hemodiafiltration device according to claim 1, wherein the means comprises a first plurality of valves in the first circuit, including a first valve upstream of the liquids pump, a second valve downstream of the liquids pump and a third valve downstream of the hemofilter with reference to the direction of flow of the dialysis liquid.

7. The hemodiafiltration device according to claim 2, wherein the blood pump is a discontinuous flow pump.

8. The hemodiafiltration device according to claim 6, wherein the discontinuous flow pump is a tubular pump.

9. A method for hemodiafiltration comprising the steps of:
(a) circulating a dialysis liquid in a first circuit through a hemofilter in a first direction of flow and receiving a blood inflow and circulating the blood in a second circuit through the hemofilter in a second direction of flow, wherein the hemofilter comprises a semi-permeable membrane separating the first and second circuits through which toxic substances from the blood in the second circuit can flow into the dialysis liquid in the first circuit when there is a first pressure gradient in the hemofilter; and
(b) injecting a substitution liquid into the dialysis liquid in the first circuit upstream of the hemofilter with reference to the direction of flow of the dialysis liquid, wherein during the injecting the second circuit upstream of the hemofilter is closed and the second circuit downstream of the hemofilter is open with respect to the direction of blood flow and the first circuit is closed downstream of the hemofilter with respect to the direction of flow of the dialysis liquid so as to create a second pressure gradient in the hemofilter that enables the substitution liquid in the first circuit to flow through the membrane into the blood in the second circuit.

10. The method according to claim 9, further comprising injecting blood into the second circuit upstream of the hemofilter with reference to the direction of flow of blood, wherein the first circuit is closed upstream and open downstream of the hemofilter with reference to the direction of flow of the dialysis liquid and the second circuit is open downstream of the hemofilter with reference to the direction of flow of blood so as to create the first pressure gradient in the hemofilter that enables toxic substances from the blood in the second circuit to flow through the membrane into the dialysis liquid in the first circuit.

11. A method for hemodiafiltrati on comprising the steps of:
(a) providing the device of claim 2;
(b) circulating a dialysis liquid in a first circuit through the hemofilter in the first direction of flow and receiving a blood inflow in the second circuit and pumping the blood through the hemofilter in the second direction of flow with the blood pump, wherein the first circuit is closed upstream and open downstream of the hemofilter with reference to the direction of flow of the dialysis liquid and the second circuit is open downstream of the hemofilter with reference to the direction of flow of blood so as to create a first pressure gradient in the hemofilter whereby toxic substances from the blood can flow through the membrane into the dialysis liquid; and
(c) during a diastole of the blood pump, injecting a substitution liquid into the dialysis liquid in the first circuit upstream of the hemofilter with reference to the direction of flow of the dialysis liquid, wherein during the injecting the second circuit upstream of the hemofilter is closed and the second circuit downstream of the hemofilter is open with respect to the direction of blood flow and the first circuit is closed downstream of the hemofilter with respect to the direction of flow of the dialysis liquid so as to create a second pressure gradient in the hemofilter that enables the substitution liquid in the first circuit to flow through the membrane into the blood in the second circuit.

\* \* \* \* \*